United States Patent [19]
Weichmann et al.

[11] Patent Number: 5,256,883
[45] Date of Patent: Oct. 26, 1993

[54] METHOD AND SYSTEM FOR BROAD AREA FIELD INSPECTION OF A MOVING WEB, PARTICULARLY A PRINTED WEB

[75] Inventors: Armin Weichmann, Kissing; Theodor Tatarczyk, Gröbenzell, both of Fed. Rep. of Germany

[73] Assignee: MAN Roland Druckmaschinen AG, Offenbach am Main

[21] Appl. No.: 959,747

[22] Filed: Oct. 13, 1992

[30] Foreign Application Priority Data

Nov. 6, 1991 [DE] Fed. Rep. of Germany ........ 4136461

[51] Int. Cl.$^5$ .............................................. G01N 21/86
[52] U.S. Cl. ..................................... 250/559; 356/430
[58] Field of Search ........................ 250/559, 562, 571; 356/237, 430; 355/68; 162/198; 101/484

[56] References Cited

U.S. PATENT DOCUMENTS

| | | | |
|---|---|---|---|
| 4,100,424 | 7/1978 | Akimoto et al. | 250/559 |
| 4,488,808 | 12/1984 | Kato . | |
| 4,555,180 | 11/1985 | Masuda et al. | 250/559 |
| 4,644,174 | 2/1987 | Ouellette et al. | 250/559 |

FOREIGN PATENT DOCUMENTS

| | | |
|---|---|---|
| 2832292 | 2/1980 | Fed. Rep. of Germany . |
| 3248928 | 7/1982 | Fed. Rep. of Germany . |
| 3605322 | 8/1986 | Fed. Rep. of Germany . |
| 3625449 | 2/1987 | Fed. Rep. of Germany . |

OTHER PUBLICATIONS

SMPTE Journal, May 1988, pp. 378-387.

*Primary Examiner*—David C. Nelms
*Assistant Examiner*—K. Shami
*Attorney, Agent, or Firm*—Frishauf, Holtz, Goodman & Woodward

[57] ABSTRACT

Information is received from an image on a moving substrate. Flash exposure is used, defining operating or exposure cycles. The reflection or a representation of the image is subdivided into a matrix having n columns and m rows or lines. The sensor is a charge coupled device (CCD), arranged to have a sensing area (11) with n columns and m rows or lines, and a storage region or section (12), likewise arranged to have storage cells of n and m columns and rows or lines. Information of any one image element, upon sensing, is shifted by a line transfer pulse by one image line. The line transfer pulses are synchronized with web movement of the substrate and operate as shift pulses. The m line, at the first transfer line shift pulse, is shifted into the first line or row of the matrix of the storage portion of the CCD. For each operating cycle, at least one line transfer pulse is used. The information of the image elements can be read out serially from the storage portion (12) at high speed. The storage portion of the CCD chip is protected against exposure to light.

18 Claims, 7 Drawing Sheets

METHOD AND SYSTEM FOR BROAD AREA FIELD INSPECTION OF A MOVING WEB, PARTICULARLY A PRINTED WEB

FIELD OF THE INVENTION

The invention relates to a method and a system to inspect a moving web, and especially a printed paper web, for appropriate printing, for example to determine if multi-color prints are all in register, in short, whether the printed output from a printing machine is in accordance with the quality expected by the printer.

BACKGROUND

Various methods and systems are known in the printing machine industry, capable of being integrated with a printing machine and to check printed products as they pass rapidly through a printing machine, typically a rotary printing machine; and, upon such inspection, to derive comparison signals between actual outputs obtained from sensors sensing the printed products and comparing those output signals with set or desired signals, to derive comparison signals for controlling, for example, variously colored inkers of inking systems, to control the register of printing stations, for example printing in different colors, and, in general, to examine and check the printed output for quality and for errors and mistakes. Sensors responsive to the printed products usually are surface sensors, capable of monitoring small or comparatively large surface areas of the printed product. Such sensors may, for example, be video cameras or line-sensors, checking the product line-by-line, for example an elongated camera apparatus. Area-type sensors have some disadvantages. In order to check a moving web, a flash arrangement must be used to "freeze" the image to be checked, so that blurred zones, due to movement of the substrate on which the image is printed, are avoided. The entire area which is being checked must be within the depth of field range of the camera equipment. This requires either large distances between the camera and the printed subject matter or the area which can be checked while maintaining sharpness is restricted. This technology, thus, is used only for macroscopic testing of a relatively small section of imaged printed material. Basically, this system is suitable for determining register as a function of a plurality of printed line or stripe elements in predetermined distances from each other, see for example the German Patent Disclosure Document DE-OS 36 25 449.

The referenced U.S. Pat. No. 4,488,808 discloses a system and a method which is intended to measure and characterize the quality of printed products during printing operation. Reflection of imaged elements, subdivided from the entire printed image or page, is sensed in a line-by-line sensing arrangement, to obtain electrical signals which are then compared with predetermined set or desired signal values. The sensor can operate continuously; it is only necessary to restrict the reception range of the sensor to a narrow region which just can accept one line for sharp reproduction from that region or line. High printing speeds require very short exposure times, which, in turn, requires high light intensity in order to provide the required light to completely control the sensors. The sensors can store the information of only one line and the termination of illumination must be so arranged that the just illuminated line can be completely read out from the sensor. The read-out frequency from sensors is limited, however, which in turn limits the maximum frequency of scanning of lines. As a consequence, the resolution of test or printed or subject matter is limited since the speed of movement of the printed subject matter is predetermined, by the operating speed of the printing machine. High operating speeds of printing machines permit digitizing of measured values to a maximum extent of eight bits, that is, 256 steps. This is not enough for high-quality optical evaluation. The system of the U.S. Pat. No. 4,488,808, thus, does not entirely overcome the disadvantages of the testing technology as heretofore known.

THE INVENTION

It is an object to provide for large area image inspection of a moving substrate, typically a printed web derived from a rotary printing machine which, in spite of high operating speed or running speed of the web, permits fine resolution of the printed subject matter to be examined with satisfactory evaluation of optical characteristics of the printed subject matter.

Briefly, the printed subject matter is subdivided into a two-dimensional matrix of n columns and m rows or lines, each intersection of a row or column forming an image element, all the image elements together defining a sensing field. In any sensing cycle, in parallel, measured values of the sensing field are obtained. Transfer pulses are generated, synchronized with movement of the web. The transfer pulses recur repetitively during any one cycle. Under control of a first line transfer pulse, the measured values of a first sensed field are shifted into a matrix store of the sensor, likewise having n storage columns and m storage rows or lines. The image areas are shifted by one row or line upon occurrence of any shift or transfer pulse and the image area values of n image areas of any one m line or row after m transfer pulses will be shifted in the first row or line of the memory. The image area values can be read out from the memory rows or lines in serial read-out.

The system, thus, obtains the image information of a portion of the printed subject matter, for each operating cycle in the form of image elements of fixed predetermined size in a two-dimensional matrix, so that the information of any one image area is shifted by a clocked, repetitively recurring transfer pulse, which occurs in synchronism with the movement speed of the printed subject matter. This line transfer pulse, thus, shifts the information by one image line. The n image elements of the $m^{th}$ line will, after m transfer pulses appear in the first line of a subsequent storage region which likewise has n columns and m lines or rows wherein it has been shifted. For each operating or exposure cycle there is at least one line transfer pulse. The information from the image elements can then be read out serially from the storage, that is, from the storage matrix system.

The arrangement permits reception over a large area without any blurring occurring due to movement of the object, that is, the printed substrate. High resolution in circumferential direction is obtained.

The clock frequency of the line transfer pulses can be very high, up to 4 MHz, for example; the command for a line transfer pulse can be given as predetermined at any time instant.

The arrangement permits a highly disturbance-resistant and error-free read-out and an apparatus and system which is reliable and has low space and energy requirements for illumination of the respective matrix elements.

DRAWINGS

DETAILED DESCRIPTION

Figure 1:
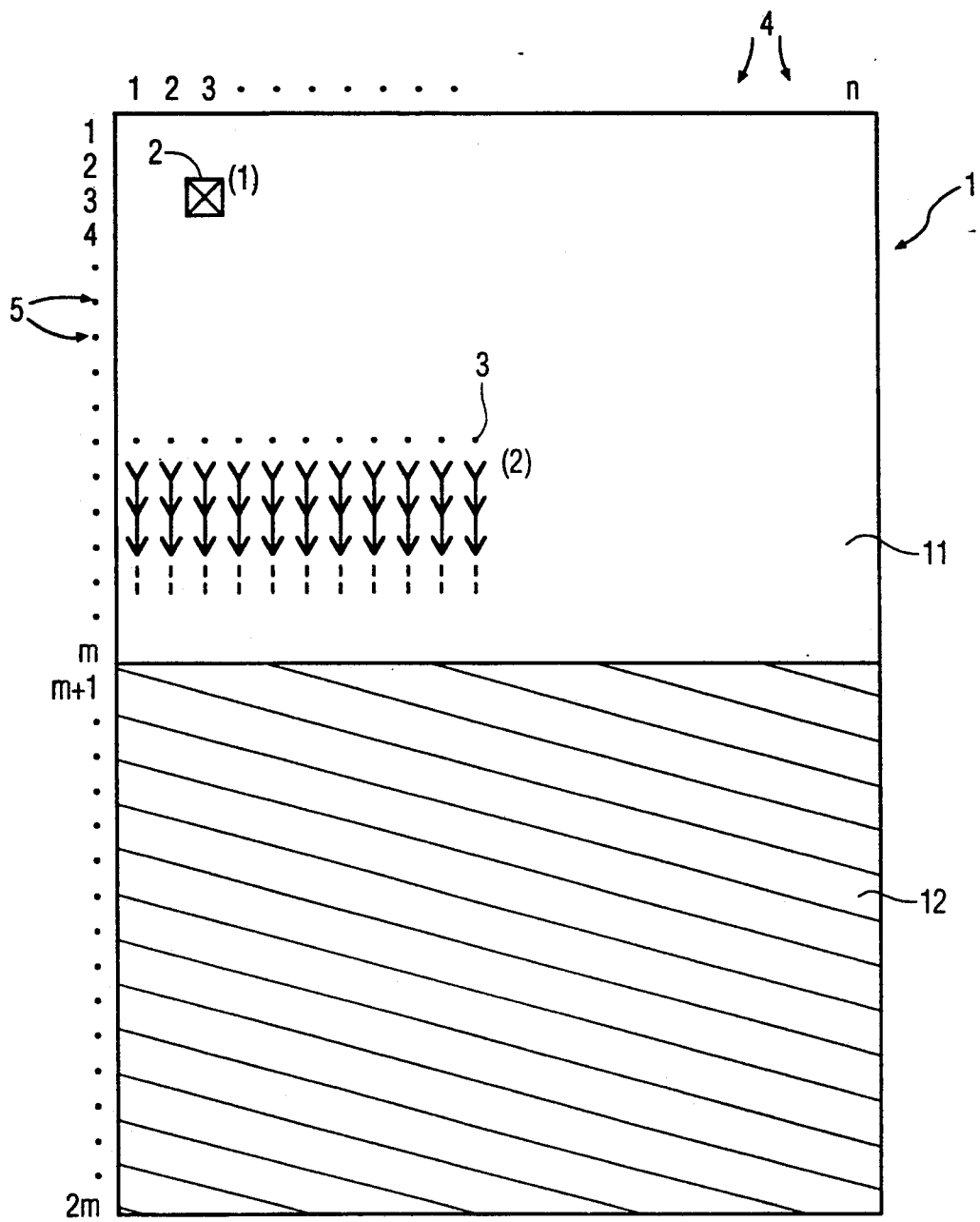
FIG. 1 is a highly schematic plan view of an area sensor in the form of a two-dimensional matrix having n columns and twice m rows or lines, and having a reception region for lines 1−m and a storage region for lines m+1 to 2 m.

An area type sensor 1, in form of a charge coupled device (CCD) sensor chip, senses image areas 2 of a substrate. The CCD sensor chip operates in accordance with a frame transfer principle. It is arranged in a two-dimensional matrix having n columns 4 and twice m lines or rows 5. Each matrix element, preferably, is formed as a square sensor cell 2, representing an image element 3. The first m rows or lines of the image area 11 are light-sensitive and form a first matrix to receive image information. The lines from (m+1) to 2 m lines form a memory 12, likewise arranged in matrix form and sequential to the first matrix. The memory 12 is protected with respect to light.

A high-intensity, for example a halogen light source 6 (FIG. 2) illuminates the substrate. To receive the actual light remission, the sensor is so arranged with respect to the light source 6 that photons in accordance with the overall area of the region 7 (FIG. 2) of the substrate to be examined or tested of the printed substrate 8 reach the sensor cells 2 via an optical system 9, 10. The optical system is shown only schematically in FIGS. 2 and 6-9. The photons can reach the sensor cells 2, in accordance with the image, within a predetermined integration time. Each sensor cell 2 is separated from an adjacent sensor cell by a surrounding voltage barrier, so that the charges in the respective sensor cells cannot run into or overlap into each other.

At the end of the reception or integration time, respectively, information from each sensor cell 2 is transferred by a line transfer pulse into the adjacent sensor cells immediately thereunder, as shown schematically in FIG. 1 by the arrows. Thus, all information of one line or row 5 is shifted downwardly. The last light-sensitive m line thus has its information shifted into the first m+1 storage sensor cell and the first line or row in the reception or sensing region 11 is completely emptied.

Between two exposure or reception cycles, it is possible to generate m line transfer commands or pulses, so that the entire image will travel into or be transferred into the storage region 12. From the storage region 12, the image values can be read out serially. This read-out can be carried out with high speed, which is dependent on the time with which the image was first taken and shifted into the storage or memory section 12, insofar as the area sensor 1 is capable of holding an image in the storage region 12 and, further, that the information of any one image has not information from a subsequent imaging cycle overwritten thereon before it has been read out.

Figure 3:
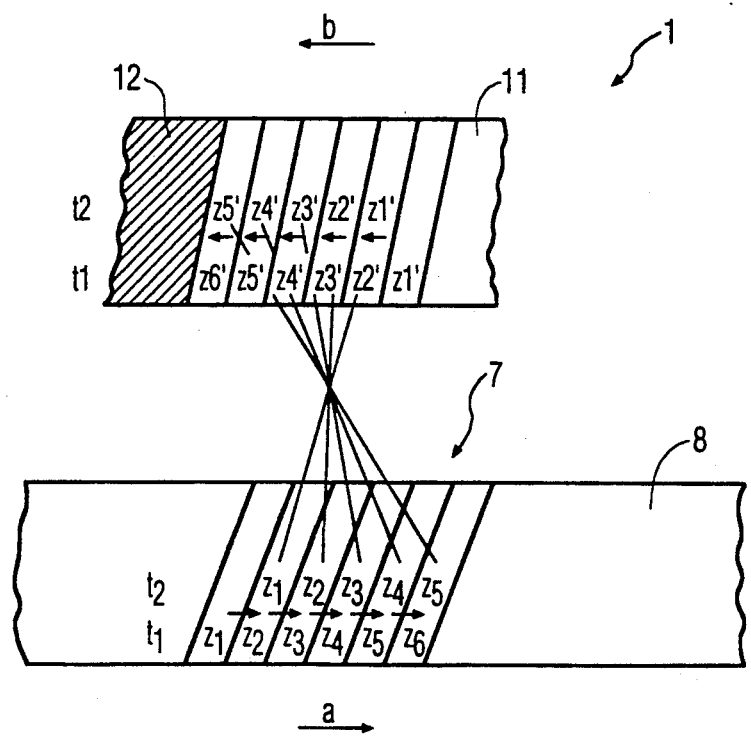
FIG. 3 illustrates sensing of printed subject matter in accordance with steps forming the subject of the present invention.

In accordance with a further and preferred feature of the invention, one line transfer pulse is generated for each operating or exposure cycle, and the exposure cycle is so synchronized with the movement speed of the printed substrate 8 that the printed substrate 8, for each operating cycle, moves by a distance which corresponds to a matrix line or row 5, multiplied by an enlargement factor of one matrix line. Each image element 3, in a subsequent reception or operating cycle, except for one additional matrix line, is then precisely imaged on the cells 2 then containing the images of elements 3 of the preceding operating cycle, so that each image element 3 is exposed and sensed a multiple number of times. FIG. 3 illustrates this arrangement graphically.

The virtually generated lines $Z_1, Z_2 \ldots Z_5$ of the section 7 of the printed substrate 8 are imaged at an imaging instant $t_1$ on the lines $Z_1', Z_2' \ldots Z_5'$ on the reception matrix 11 of the sensor 1. At the next exposure instant $t_2$, the printed substrate has been moved by one virtually generated line of the portion 7. The lines $Z_1$ to $Z_5$ appear to move in opposite direction, see arrow a with respect to the direction of the lines $Z_1' \ldots Z_5'$, see arrow b. This multiple exposure by a factor of k reduces the required light intensity for each complete exposure to 1/k in the example of FIG. 3 by 1/5.

This arrangement has the advantage of better stability of the measuring results with respect to short-time variations in operating speed of the printed substrate 8. Multiple exposure provides for an inherent local as well as temporal averaging, which, upon changes in operating speed of the substrate, results in a summation extending about slightly varying but overlapping imaging zones or regions or, respectively, over slightly different exposure or illumination times. This slightly reduces the sharpness of the image; it prevents, however, that substantial localized differences between actual and desired or command values occur which prevent or at least interfere with direct comparisons. Additionally, it permits a simplified processing of the data when making a comparison between actual and set or desired values, since well-known filter functions, for example a dynamic averaging, well known from the general technology of recognition, need not be used.

After m lines 5 have been received, the memory 12 of the sensor 1 is full. It can be read out, in accordance with any desired read-out speed and accuracy of read-out at a rate which is very high, so that a line 5 can be read out before the next line transfer pulse is received. This permits continuous operation, that is, the number of the lines received is not limited by the storage capacity of the storage matrix 12. Alternatively, the reception cycle can be stopped and the data can be read out asynchronously, but slower, for example with a higher accuracy. Accuracies of 12 bits, that is 4096 steps, or 16 bits providing for 65,536 steps, can be evaluated. Thus, an area sensor 1 can receive an image region having a number m of storage lines; these sensor stored lines must be read out before a new operating or exposure cycle can start.

Figure 2:
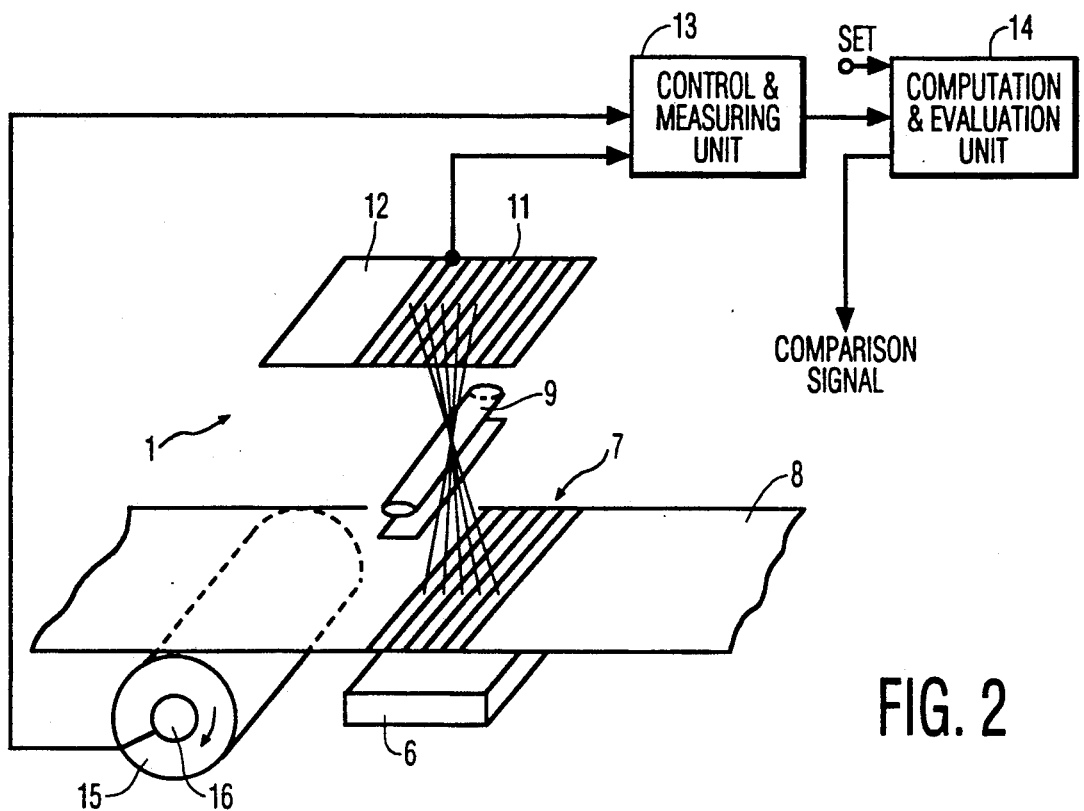
FIG. 2 is a schematic drawing of a large area printed image inspection system.

The system to carry out the above method is seen, highly schematically, in FIG. 2. The area sensor 1 is a CCD sensor chip, as described in detail in connection with FIG. 1. It is coupled to a control and measuring electronic unit 13 which, in turn, is coupled to a computation and evaluation unit 14. A substrate web 8, to be examined, for example the printed output from a printing machine, is moved parallel to the area sensor 1, as seen in FIG. 2. The control and measuring unit 13 is synchronized by an angle encoder 16 coupled to a roller 15 rotating in synchronism with the movement and at the same speed as the printed web 8. An optical system 9 to image the image information from the printed substrate 8 is provided. The light source 6, to illuminate the portion 7, is located in a straight line with respect to the optics 9 and the area sensor 1.

If the localized resolution obtainable by imaging sensor elements 2 is not required, a group of image elements 3, in either line direction, or column direction, or both, can be used. Such grouping can be done directly on the CCD sensor chip, which increases the light sensitivity by a factor corresponding to the number-of the imaging elements 3 grouped together. At the same time, the read-out speed, with the same read-out frequency, is increased, since only one value for each group must be obtained. Rather than grouping the imaging areas on the CCD sensor chip, grouping can be carried out by software after digitizing. Thus, rather than increasing the light sensitivity in the read-out speed, the accuracy of the output values is increased by statistical averaging, It is, of course, possible to combine both grouping arrangements.

Figure 4:
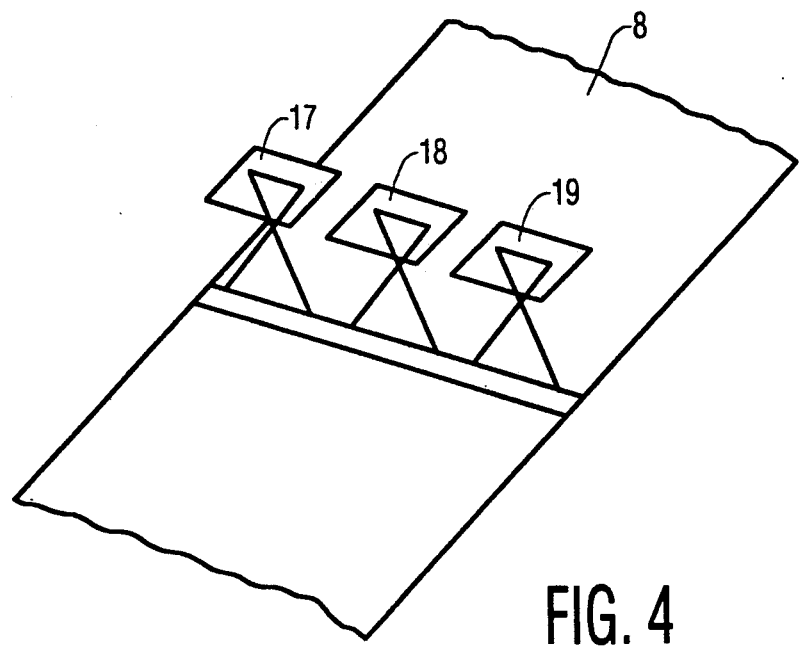
FIG. 4 is a schematic view of an area sensor having a plurality of charge coupled device (CCD) sensor chips located transversely across a printed substrate.
Figure 5:
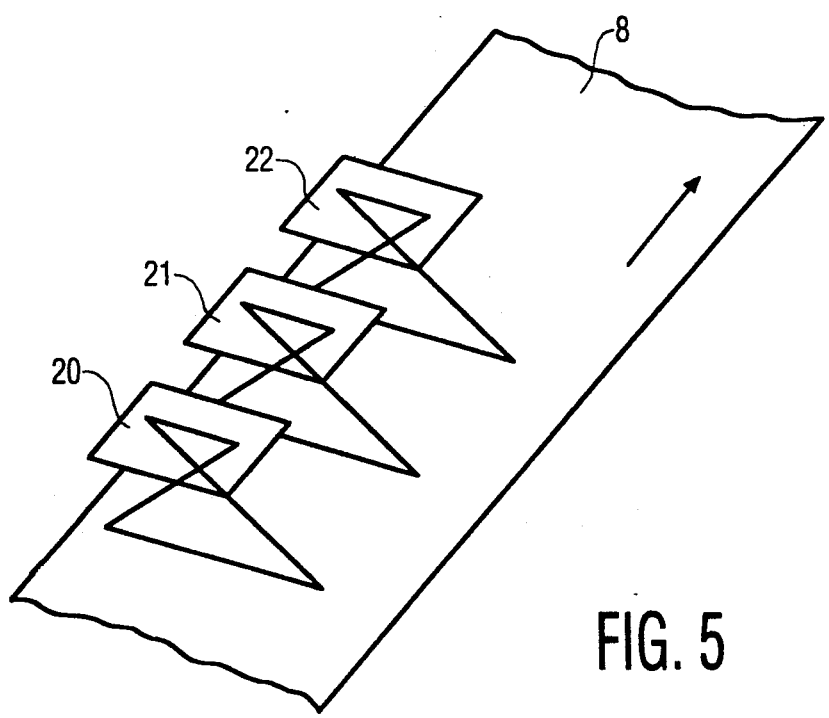
FIG. 5 is a schematic drawing showing a purality of CCD sensor chips located serially in the direction of movement of a printed web.
Figure 6:
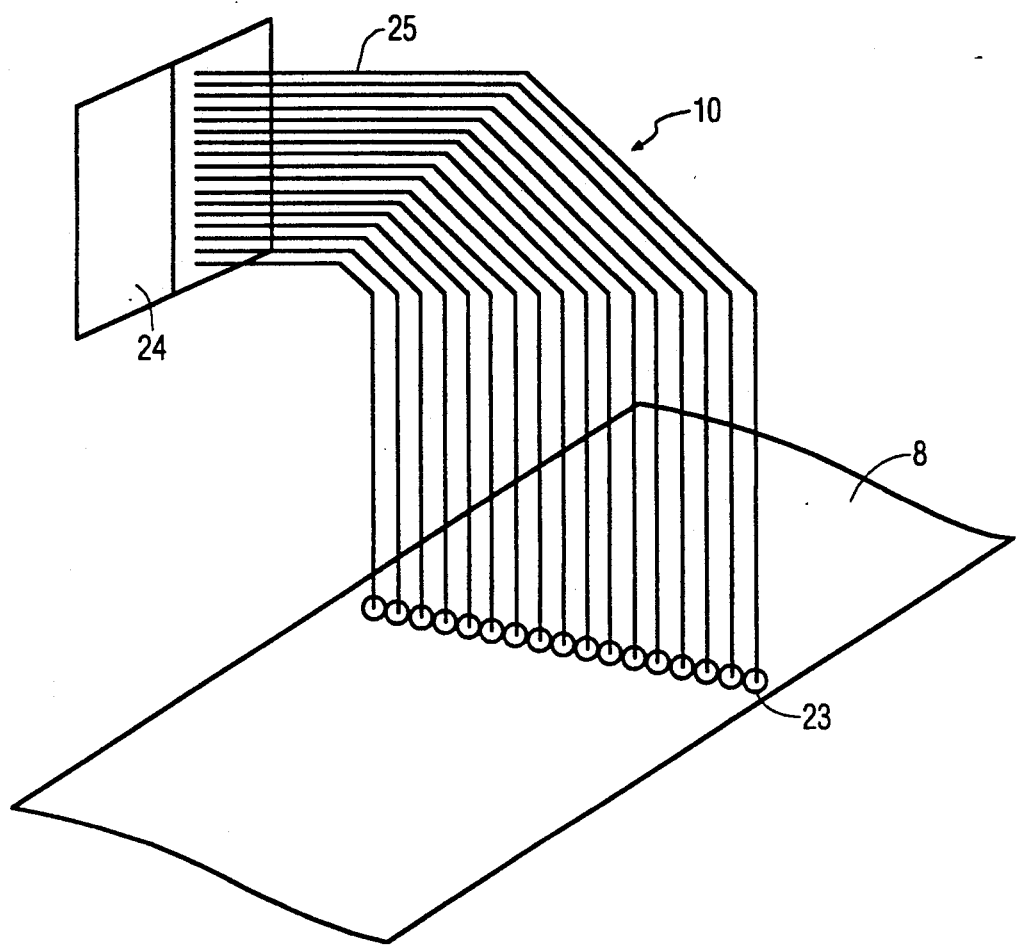
FIG. 6 is a schematic view of another system for wide area imaging of printed subject matter, using glass fiber optics.
Figure 7:
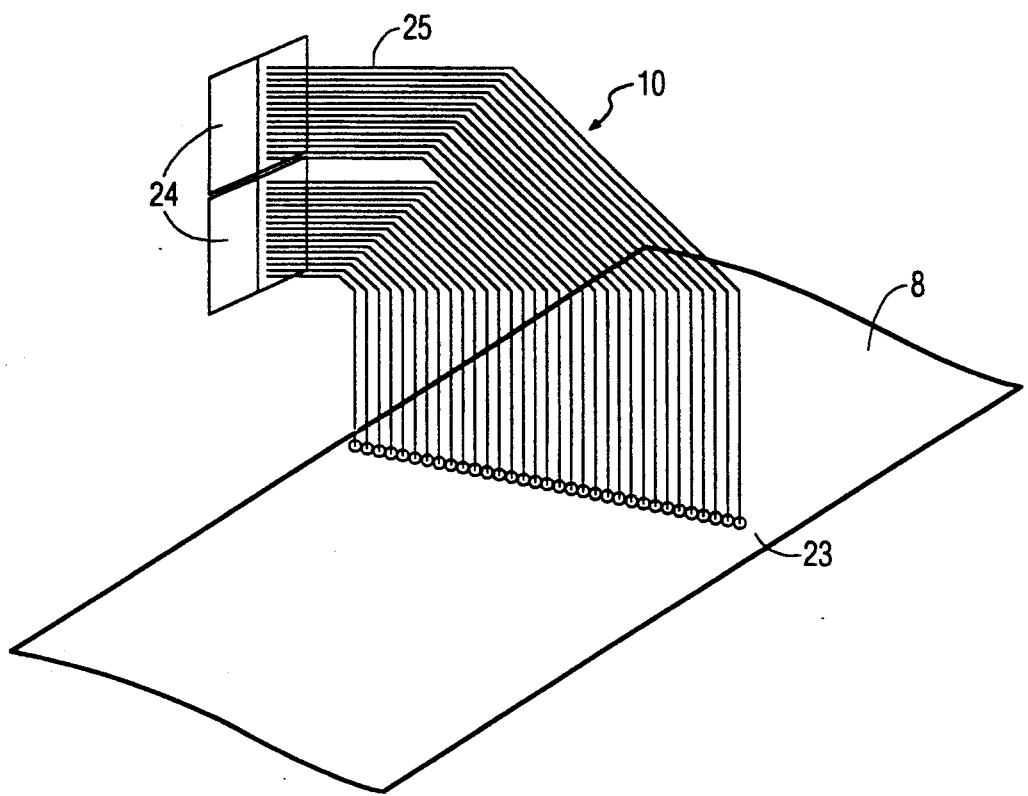
FIG. 7 illustrates another arrangement for inspecting a moving web using glass fiber optics and coupled to a plurality of CCD sensor chips operated in parallel.

To increase the resolution, the system illustrated schematically in FIG. 4 can be used. The resolution of images on the printed substrate 8 is improved by using a plurality of CCD sensor chips 17, 18, 19 and operating them in parallel. A plurality of sensor chips 20, 21, 22 can also be serially placed, as seen in FIG. 5. If exposure and sensing is temporally shifted, either the region covered, in the running direction of the printed substrate 8, can be increased, or the resolution in the direction of movement can be increased; alternatively, by providing different color filters within a region 7, the imaged areas on the substrate 8 can be sensed with respect to different filter ranges or colors.

Figure 8:
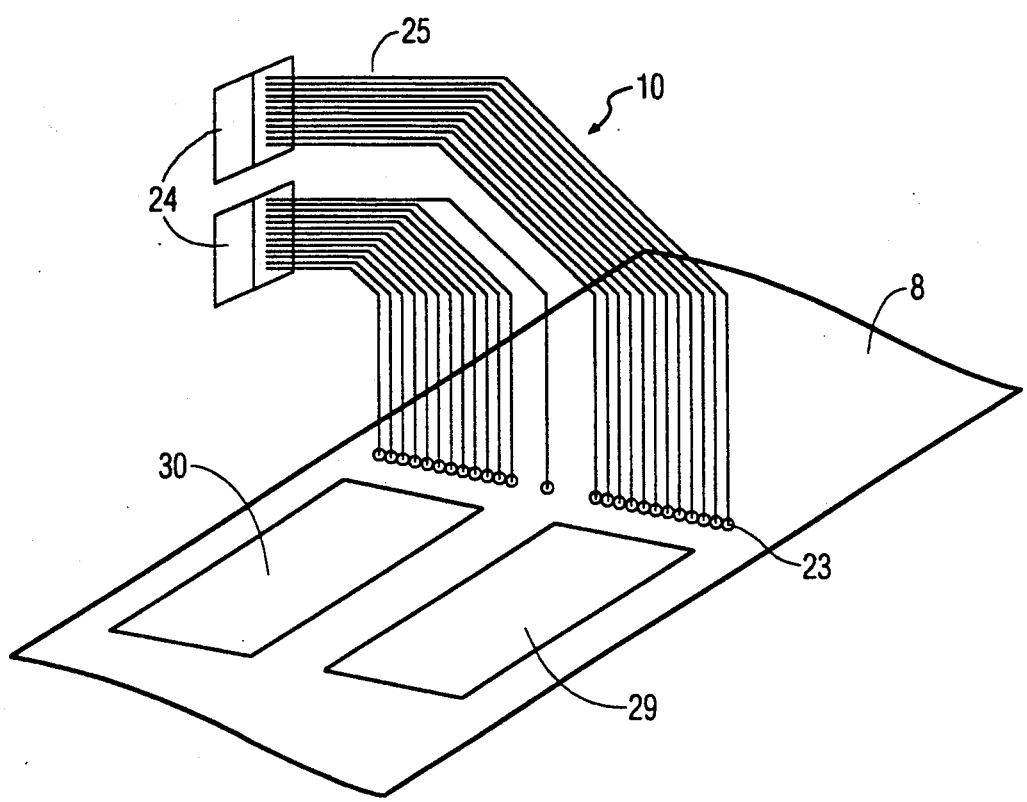
FIG. 8 illustrates another arrangement for wide area printed subject matter inspection in which the glass fiber optics is correlated with the subject matter to be printed.

In accordance with another preferred arrangement, a glass fiber optic 10 is used rather than customary optical system 9, see FIGS. 6–9. Glass fiber inputs 23 (FIG. 6) are located in sensing relation to the substrate 8. These inputs 23 can be positioned at equidistant spacings or steps in form of lines, see FIG. 6; alternatively, they can be located as shown in FIG. 8 in accordance with subject matter, for example related to printed subject areas 29, 30 and only one chip related to a margin or intercolumnar region between the areas 29, 30. Alternatively, the glass fibers 25, coupled to the fiber receptor inputs 23, can be associated with a plurality of sensor chips 24, see FIG. 7, connected together either in lines or arranged by subject matter (FIG. 8). One or more filters can be interposed between the sensor chip or chips 24, or integrated in the fiber optics 25, or a reception terminal 23 thereof. These filters may, for example, be infrared filters, specifically designated color filters for standard color ranges, or filters compensating or adapting the sensor outputs to visual color sensitivity. Grouping of image elements will be determined by the dimensions of the glass fibers 25 which, preferably, are differently made for different applications. For extremely fine resolution, that is maximum obtainable resolution, the fibers are selected to be so small or fine that for each image element 3 of the area sensor 24 one fiber 25 is used. If a less accurate resolution is acceptable, a thick fiber is used, or a plurality of thin ones which are bundled together in order to image a comparatively large area on a comparatively large area of the sensor. Thus, high accuracy of measurement and fine resolution can be obtained or high light sensitivity or reflectivity can be measured.

FIG. 8 illustrates a variation in which available sensor surfaces of one or more—in FIG. 8 two—sensor chips can be more effectively utilized than in the previously illustrated examples, by so placing the sensors 25 that they are closer together at the imaged areas 29, 30 which are important to be measured than in margin areas as illustrated by the centrally positioned fiber terminal 23 and the associated fiber light guide connected to the lower sensor 24.

Figure 9:
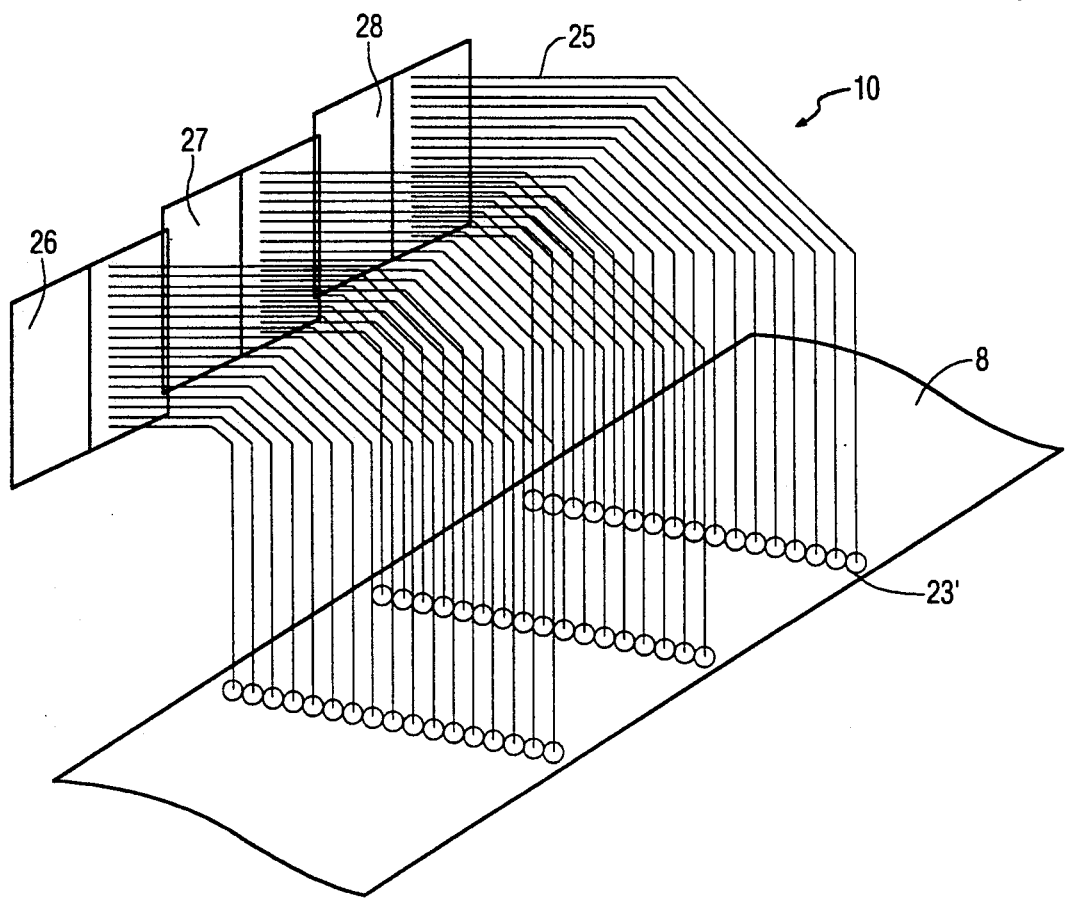
FIG. 9 illustrates another arrangement for wide area inspection of printed subject matter using glass fiber optics with integrated filters.

FIG. 9 illustrates another and suitable variation or embodiment, which is preferred for simultaneously receiving outputs representative of different characteristics of the printed image. If, for any one image which is to be received from the printed substrate, a plurality of fibers, as seen in FIG. 9 three fibers, are located, locally offset with respect to each other, conducted, respectively, by the guides 25 to respective tips 26, 27, 28, and in which each of the fibers has different transmission characteristics, for example by incorporating a filter therein, a plurality of filtered outputs can be obtained at the same time. The fiber inputs 23' can have a filter integrated therein.

The system and method, thus, permits receiving information from an image on a moving substrate, for any one operating cycle, by subdividing and receiving the image in form of a two-dimensional matrix having n columns and m rows or lines. The information of any one entire image element is shifted by a line transfer pulse by one image line . The line transfer pulses are synchronized with the web movement of the substrate, and operate as shift pulses. The m line, at a first line transfer shift pulse is shifted into the first line or row of the matrix of a storage element 12 coupled to the reception CCD sensor portion 11. The storage portion 12 of the CCD sensor likewise has n columns and m rows. For each operating cycle, at least one line transfer pulse is used. The information of the image elements can be read out serially from the storage portion. Each one of the two-dimensional matrices of the sensor is represented by a sensor cell; the first group of m lines are light-sensitive, and the second group of m lines are protected against light exposure, so that the sensor chip itself has an exposure or reception region and a memory or storage region.

Various changes and modifications may be made and any features described herein may be used with any others, within the scope of the inventive concept.

We claim:

1. A method of continuous broad-area field inspection of image areas (7) on a moving substrate (8), particularly a printed substrate web received from a rotary printing machine during operation of the printing machine, in which measured values representative of the respective image elements (3) of image elements of the measured areas are obtained in form of electrical signals, for comparison with reference or setting signals and derivation of comparison signals, said method comprising, in accordance with the invention, determining a sensing or operating cycle;

subdividing the image area (7) into image elements (3) and arranging the image elements in a two-dimensional matrix having n columns (4) and m rows or lines (5), so that said m rows or lines and said n columns of the image areas will define a sensing field (11);

obtaining, in any sensing cycle, in parallel, the measured values of the sensing field (11);

generating, during any sensing or operating cycle, at least one repetitively recurring line transfer pulse, synchronized with the movement of the web;

shifting, under control of said line transfer pulse the measured values of the image elements (3) by one row or line (5);

storing the n image elements of the $m^{th}$ line after m line transfer or shift pulses in a first line of a two-dimensional matrix store or memory (12), said two-dimensional store or matrix having n columns (4) and m rows or lines (5), whereby any line m', after m line transfer pulses, will be stored at a storage location line of m+m' in the memory (12), wherein, for each operating or sensing cycle, at least one line transfer or shift pulse is generated; and reading out the measured values representative of the signals derived from the image elements (3) from the store or memory (12), line-by-line.

2. The method according to claim 1, wherein said reading-out step comprises serially reading out the store or memory line-by-line.

3. The method according to claim 1, wherein said step of obtaining measured values representative of the image elements (3) comprises obtaining measured values in a charge coupled device (CCD) (1) having a sensing region (11) and a storage region (12), said sensing region being exposed to said image areas (7) and said storage region being light-impervious and forming said store or memory.

4. The method according to claim 1, wherein said line transfer or shift pulses are sequentially generated during each sensing or operating cycle, and measured values representative of the entire image area (7) are transferred into the store or memory (12) before occurrence of the next subsequent sensing or operating cycle, for read-out from the store or memory (12) serially, line-byline, before, during a subsequent sensing or operating cycle, the subsequent image area can override measured values in image elements of the preceding sensing or operating cycle.

5. The method according to claim 1, wherein one line or shift transfer pulse is generated fro each sensing or operating cycle;

the sensing or operating cycle being so synchronized with the movement speed of the substrate (8) that, for each operating cycle, the substrate moves by a distance corresponding to the height of one matrix line multiplied by an enlargement factor; and in which any image element (3), imaged and generating a measured value of a subsequent sensing or operating cycle, except for one additional matrix row or line, is imaged on a sensor cell (2) at a position corresponding to the image elements of the preceding operating cycle, and shifted by one matrix line, so that any one image element (3) is repetitively imaged at sensor cells sequentially responsive to the same image element.

6. The method according to claim 1, wherein the reading-out step to read out measured values from the store or memory (12) is carried out at a read-out speed which is fast enough to read out n image elements (3) for each line transfer or shift pulse, so that one line (5) is read-out before the next line transfer or shift pulse is generated.

7. The method according to claim 1, wherein the read-out step to read out the measured values from the store (12) comprises reading out the measured values of the image elements (3) between two sequential line transfer or shift pulses.

8. The method according to claim 1, wherein the step of obtaining measured values comprises imaging a plurality of image elements (3) at least in one of the matrix directions (n or m, or both) unto one sensing element, to permit lower imaging light intensity but resulting in lesser resolution of the imaged aread.

9. An apparatus for continuous broad area field inspection of image areas (7) on a moving substrate (8), particularly a printed substrate web received from a rotary printing machine, during operation of the machine, said apparatus carrying out the method of claim 1, and having a light source (6) illuminating the image area (7);

a receiving sensor (11);

a control and measuring unit (13) and a computation and evaluation unit (14) coupled to the receiving sensor (1);

synchronizing means (15, 16) coupled to the moving substrate and generating substrate speed pulses, wherein, in accordance with the invention, the receiving sensor (1) comprises an area sensor (1, 17-22, 24, 26-28), having its area subdivided and arranged in form of a two-dimensional matrix n columns (4) and twice m rows or lines (5), wherein each matrix element forms a sensor cell (2), and wherein the first m lines or rows are light-sensitive and positioned in sensing relation with respect to the image areas (7),and the second m lines (5) are protected with respect to light reception, said area sensor forming thus a reception region (11) and a memory or storage region (12); and wherein optical means (9, 10) are provided for imaging image elements (3) the imaged areas (7) on the reception region (11) of the receiving sensor (1).

10. The apparatus according to claim 9, wherein said receiving sensor (1, 17-22, 24, 26-28) comprises a charge coupled device (CCD) sensor chip, operating in accordance with the frame-transfer principle;

and wherein said optical means (9, 10) is positioned between the image areas (7) of the moving substrate (8) and said CCD sensor chip, wherein the CCD sensor chip and the moving substrate are located parallel to each other.

11. The apparatus according to claim 7, wherein a plurality of parallel coupled receiving sensors (17, 18, 19) are provided, each comprising a CCD sensor chip, whereby resolution of sensing of the image areas is improved.

12. The apparatus according to claim 7, wherein a plurality of area sensors (20, 21, 22, 24, 26–28) are provided, located I serially, in the direction of the moving substrate (8) to increase the size of the image areas (7), said sensors comprising CCD sensor chips and being coupled to said control and measuring unit and computation and evaluation unit.

13. The apparatus according to claim 10, wherein the optical means comprises a glass fiber optics (10).

14. The apparatus according to claim 13, wherein the glass fiber optics (10) includes input means (26) located equidistantly spaced across a width dimension of the substrate (8);

and wherein the glass fiber optics includes glass fibers (25) which are positioned in optical signal transfer relationship to the receiving sensor (24, 26, 27, 28) in line-by-line arrangement.

15. The apparatus according to claim 14, wherein the glass fiber optics includes glass fiber input elements (23) arranged in accordance with distribution of image areas on the substrate (8) across the width of the substrate, and coupled to the receiving sensor (24) in line-by-line optical relationship.

16. The apparatus according to claim 13, wherein the glass fiber optics includes receiving means (23) and fiber transmission elements (25) coupled to the receiving means;

and wherein a plurality of receiving means are associated to sense the image areas on the substrate, and a plurality of sensing means, each formed by a CCD sensor chip (26, 27, 28), is provided, selected glass fiber elements (25) being coupled to selected ones of the plurality of CCD sensor chips.

17. Method of continuous broad area field inspection of image areas (7) on a moving substrate (8), particularly a printed substrate web received from a rotary printing machine, during operation of the printing machine, comprising determining a sensing or operating cycle;

subdividing the image area (7) into image elements (3);

arranging the image elements in a two-dimensional matrix having n columns (4) and m rows or lines (5), said n columns and m rows or lines defining a sensing field;

sensing the image areas, in any sensing cycle, and storing the sensed image area values in a memory or store, said memory or store having n memory columns and m memory rows or lines, corresponding to said columns and rows or lines of the image elements of the image area;

generating, during any sensing or operating cycle, at least one repetitively recurring line or shift transfer pulse, synchronized with movement of the substrate (8);

shifting the image areas by one row or line upon occurrence of any shift or transfer pulse, to shift the image area values of n areas of m lines after m transfer pulses into the rows or lines of the memory or store (12); and serially reading out the image area values from the memory or store (12) line-or-row by line-or-row.

18. The method according to claim 17, wherein said step of sensing the image areas comprises imaging the image areas on a charge coupled device (CCD) chip having sensor cells (2) arranged in a two-dimensional matrix with n columns (4) and two groups of m rows (5), in which each matrix element represents a sensor cell (2), the CCD sensor chip operating in accordance with the frame-transfer principle, and the first group of m rows or lines being light-sensitive and the second group of m rows or lines (5) being protected against light to form a store or memory (12) for reception of shifted sensing signals upon carrying out said storing step.

* * * * *